United States Patent [19]

Rice

[11] 4,410,700
[45] Oct. 18, 1983

[54] PREPARATION OF CHIRAL 1-BENZYL-1,2,3,4-TETRAHYDROISOQUINOLINES BY OPTICAL RESOLUTION

[75] Inventor: Kenner C. Rice, Rockville, Md.

[73] Assignee: The United States of America as represented by the Department of Health and Human Services, Washington, D.C.

[21] Appl. No.: 265,469

[22] Filed: May 20, 1981

Related U.S. Application Data

[63] Continuation-in-part of Ser. No. 165,690, Jul. 3, 1980, abandoned.

[51] Int. Cl.³ .................................................. C07D 217/20
[52] U.S. Cl. .................................. 546/149; 546/44; 546/18; 546/74; 564/139
[58] Field of Search ........................................ 546/149

[56] References Cited

U.S. PATENT DOCUMENTS 3,810,899  5/1974  Mohacsi et al. ............... 246/149
3,855,227 12/1974  Hollander et al. ............ 260/286
3,894,027  7/1975  Sohar et al. .................. 260/286
4,194,044  3/1980  Mohacsi ........................ 546/146

FOREIGN PATENT DOCUMENTS 201520  4/1956  Australia ...................... 546/149
474229  4/1972  Japan ........................... 546/149

OTHER PUBLICATIONS

Bossi, et al., "Synthesis . . . Isoquinoline Series . . . ", *Helv. Chim. Acta*, 44, 1558–1565 (1961).
Kirschner, et al., "Pfeieffer Effect to Resolution . . . ", *Chem. Abs. 67*; 5562u.
Bosman, et al., "Synthesis of Racemic and Optically Active Codiene and Morphine . . . ", *Royal Netherlands Chem. Soc. 97*, pp. 127–130.

*Primary Examiner*—Donald G. Daus
*Assistant Examiner*—G. M. Hendricks
*Attorney, Agent, or Firm*—John S. Roberts, Jr.

[57] ABSTRACT

In a short total synthesis of morphinan compounds, derivatives of 1-benzyl-1,2,3,4-tetrahydroisoquinoline are produced. Certain of these compounds, although highly aromatic and functionalized, can be optically resolved. The optically active enantiomers can serve as important intermediates for both natural and unnatural opioids.

1 Claim, No Drawings

PREPARATION OF CHIRAL 1-BENZYL-1,2,3,4-TETRAHYDROISOQUINO-LINES BY OPTICAL RESOLUTION

CROSS REFERENCE

This application is a continuation in part of U.S. application Ser. No. 165,690, filed July 3, 1980, now abandoned.

PRIOR ART

In addition to the prior art statement in the parent application, the following references are pertinent:

U.S. Pat. Nos. 2,819,272, DenHollander (Hoffmann-LaRoche), and 2,915,479, DenHollander (Hoffmann-LaRoche), pertain to octahydro derivatives and they differ by the fact that they have only one aromatic ring and the present invention has two. Both aromatic rings are more highly functionalized in the series of the present invention. There is no indication of carryover of teaching from the known patents to the present application.

U.S. Pat. No. 3,914,232, Mohacsi et al. (Hoffmann-LaRoche), deals with the racemization of octahydroisoquinolines. This differs from the present invention in that it is much less functionalized system and has only one aromatic ring whereas the present invention has two.

British Pat. No. 1,330,581, Merck & Co., is of general interest.

Yamaguchi et al., Yakugaku Zasshi, 82:552 (1962), abstracted in Optical Resolution Procedures for Chemical Compounds, Volume 1, Amines and Related Compounds, by Paul Newman, Optical Resolution Information Center, Riverdale, N.Y., page 398—the solvent and conditions for this isoquinoline differs substantially from the present invention.

Kamentani et al., J. Chem. Soc., 1968, pp. 1619–1620, deals with racemization of a tertiary amine rather than the secondary amine of the present invention.

Kametani et al., Heterocycles, Vol. 5, 1976, pp. 649–668.

Beyerman et al., Recl. Trav. Chim. Pays-Bas, 97:127 (1978) describes a process directed to a rather esoteric method which additionally uses time encompassing protecting intermediates.

The following references discuss the importance of (+)-opioids for antitussive agents and neuropharmacological research tools:

Takagi et al., Yakugaku Zasshi, 80:1506 (1960).

T. T. Chan and L. S. Harris, J. Pharm. Exp. Ther., 215:668 (1980).

I. Iijima, et al., J. Med. Chem., 21:398 (1978) and references cited therein.

BACKGROUND OF THE INVENTION

The present application relates to production of chiral intermediates for total synthesis of (−)- and (+)-opioids by the method disclosed in U.S. patent application Ser. No. 165,690, filed July 3, 1980. Since all medically important opium derivatives, including thebaine, can be manufactured from intermediates prepared in the above-mentioned disclosure, the simple and effective methods described below for synthesis of chiral precursors are of fundamental importance. In addition to affording intermediates for production of (−)-opioids (natural), the present disclosure also permits synthesis of intermediates useful for preparing (+)-opioids which are of importance as antitussive agents and neuropharmacological research tools.

The synthesis outlined for the total short synthesis of dihydrothebainone, dihydrocodeinone, and nordihydrododeinone is shown schematically in the following outline.

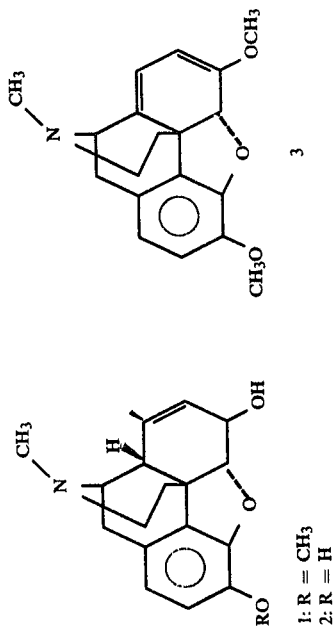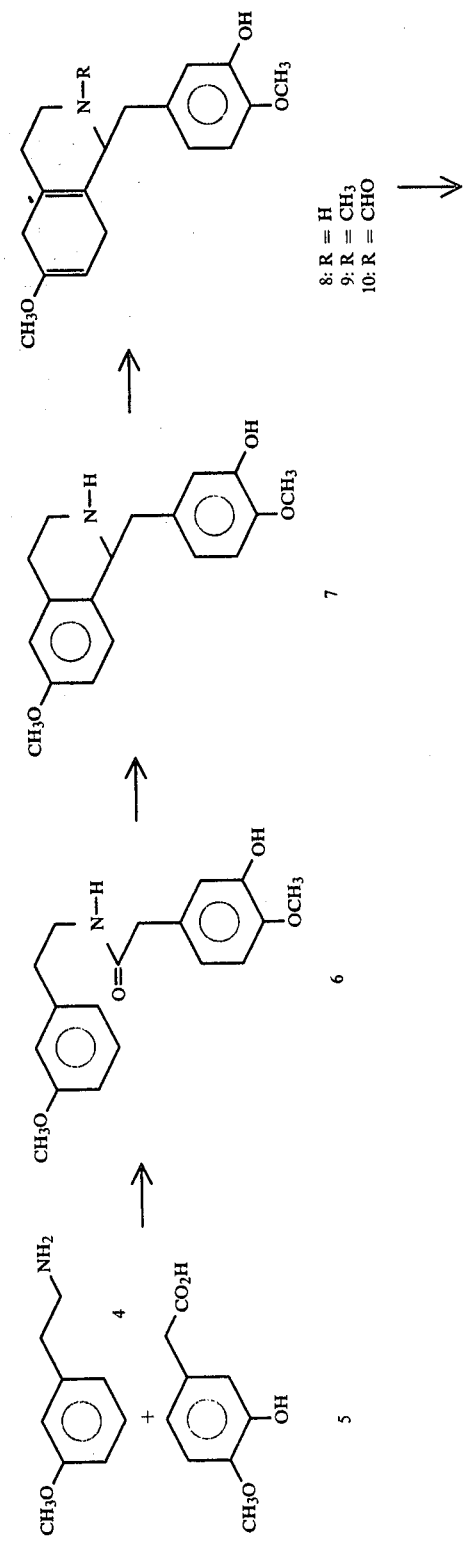

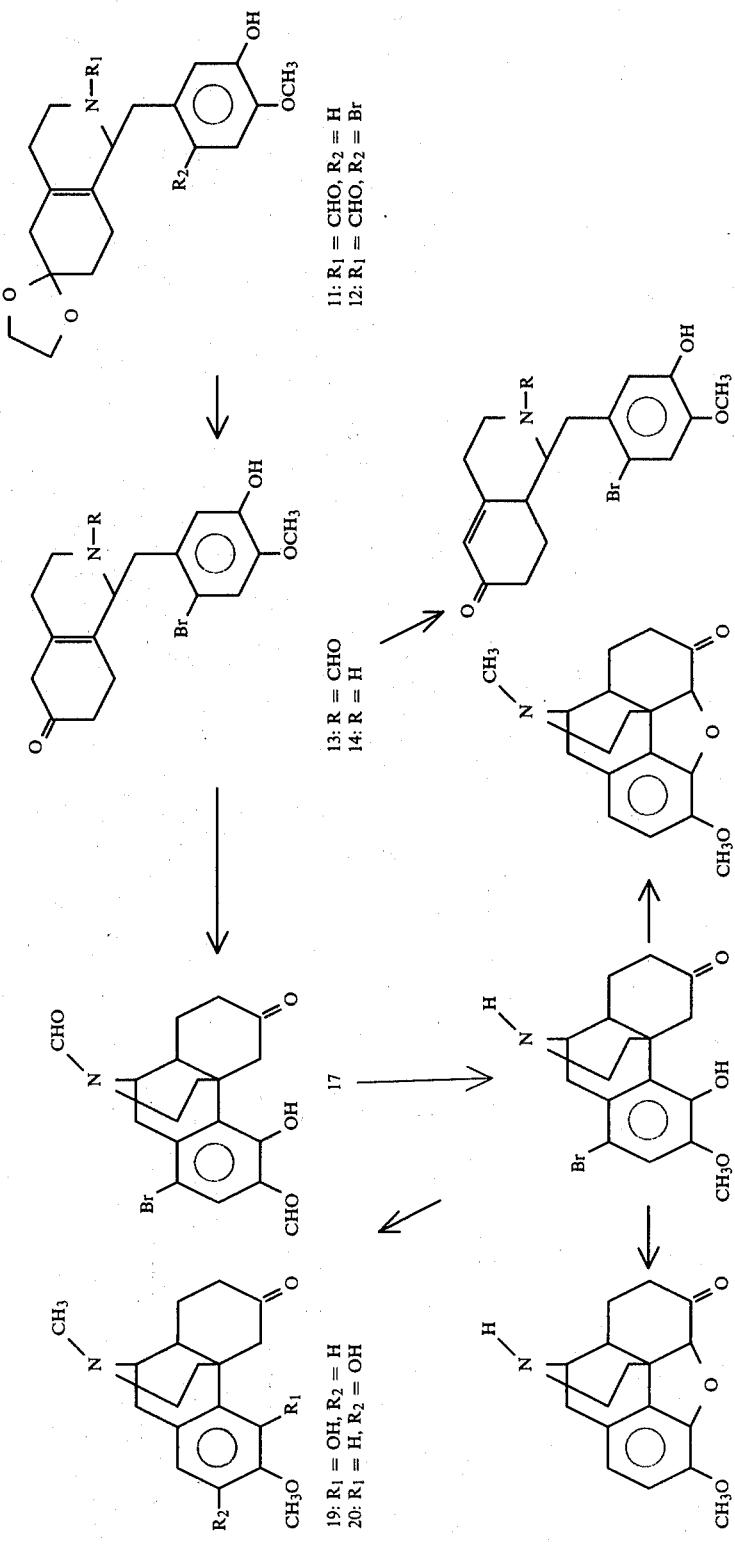

As a general summary of the above chart, the following general description is made commencing with codeine (1).

Racemic dihydrothebainone (19), nordihydrocodeinone (21) and dihydrocodeinone (22) were synthesized in high overall yield from 3-methoxyphenethylamine (4), via the key intermediate (±)-1-bromonordihydrothebainone (18); the route utilized unprotected phenolic intermediates, involved directed Grewe-type cyclization and for 21 and 22, exploited novel oxide bridge closure in the N-nor series.

Heating a mixture of amine (4) and pure acid (5) afforded amide (6). Cyclization of 6 generated an aqueous solution of the 1,2-dihydro derivative of 7, not shown on the chart. This derivative is the starting point for the novel asymmetric synthesis of this invention. (The possibility for resolution of racemic tetrahydroisoquinoline 7 is suggested in the parent application.) Birch reduction with lithium and ammonia afforded 8. Refluxing 8 with PhOCHO or chloral gave 10. A solution of 10 and ethylene glycol generated a solution of ketal 11 and subsequently bromoketal 12 was produced. Grewe-type cyclization produced 17. Refluxing 17 in MeOH-aqueous HCl yielded 18. 19 is available from 17 by hydrogenation in the presence of formaldehyde. Synthesis routes from 18 yield 19, 21, and 22. Specific details are found in the parent application, incorporated by reference.

Conversion of (−)-19 to (−)-thebaine (3) and (−)-codeine (1) and facile O-demethylation of the latter to (−)-morphine (2) provide a practical total synthesis of these natural alkaloids.

SUMMARY OF THE INVENTION

The present invention provides for a facile optical resolution of phenolic 1-benzyltetrahydroisoquinoline 1' and ethers 2' and 3' (prime numbers refer to the following chart of compounds). This resolution thus makes available two optical forms and thereby the synthesis route previously discussed is utilized for the production of both natural (−)- and unnatural (+)-opioids.

The concept of formation and chromatographic separation of diasterisomers is well known. However, the compounds of interest herein are, unlike the prior art, highly aromatic and highly functionalized.

Optical resolution has also been empirical and highly individualized. Among the most difficult enantiomers to resolve are the phenolic secondary amines in the 1-benzyl-1,2,3,4-tetrahydroisoquinoline series. Even ten years ago resolution of these compounds depended on conversion to benzyl ethers and resolution therefrom. The prior art [Yamaguchi, H., et al., Yakugaku Zasshi, 82, 555 (1962)] for a phenolic secondary amine shows an acid and solvent quite different from the present invention.

It is well recognized that salt formation and solubility parameters are very critical and much experimentation is necessary to find the proper combination for each individual resolution.

The present invention also encompasses racemization of either enantiomer of 1' and derivatives so that, if desired, one enantiomer can be produced to the exclusion of the other by recycle of the racemate. Racemization can be accomplished by catalytic hydrogenation of the chiral 1-benzyl-1,2,3,4-tetrahydroisoquinoline with metal catalysts such as palladium, platinum, nickel and cobalt. Platinum and palladium catalysts in solvents such as alkanoic acids, ethers, and hydrocarbons are preferred. Simple filtration of the catalysts and workup by evaporation of the solvent affords the racemate in high chemical yield. Also, oxidation of 1-benzyltetrahydroisoquinolines, lower alkoxy and acyloxy derivatives (see chart) with reagents such as sodium hypochlorite, sodium hypobromite, and lower alkyl hypochlorites and hypobromites, and treatment with base to give dehydro intermediate of type 4'-6', followed by reduction with sodium cyanoborohydride or sodium borohydride can be used to effect racemization of 1'-3'. Synthesis of 4' and sodium cyanoborohydride reduction of 4' to 1' were described in application Ser. No. 165,690 Rice, ante.

A further aspect of the invention consists of asymmetric reduction of intermediates 4'-6' to give 1'-3'. For this reduction process either asymmetric catalytic hydrogenation or chemical reduction may be used.

For catalytic reduction, hydrogenation of 4'-6' using rhodium complexes with chiral ligands such as DIPAMP, CHIROPHOS or NORPHOS (available from Reaction Design, Hillside, N.J.) are used in alkanols, alkanol ethers, water or mixtures thereof. U.S. Pat. No. 3,849,480 describes asymmetric hydrogenation, catalysts and process steps. These catalysts have been used quite successfully in asymmetric hydrogenation of azalactones to eventually afford optically active amino acids. Intermediates of the type 7'-9' which are easily available from 4'-6' by standard methods are ideal for asymmetric hydrogenation to the N-acetyl derivatives of 1'-3'. The 1'-3' can then be obtained by standard acid or alkaline hydrolysis of the acetyl group(s) or the chiral N-acyl derivatives can be utilized directly for further reaction.

For chemical reduction of 4'-6' to 1'-3', chiral boranes such as diisopinocampheylborane derived from the readily available (+) and (−)-pinene and other chiral boranes may be employed in ether-type solvents such as tetrahydrofuran, glyme (dimethyl ether of ethylene glycol) and diglyme. Also, chemical reduction with sodium borohydride and sodium cyanoborohydride in reaction media such as aqueous or aqueous alcoholic chiral tartrate-phosphate buffer systems may be employed. By utilization of either (+)- or (−)-tartaric, malic or other optical pairs of organic acid either enantiomer of 1'-3' may be obtained.

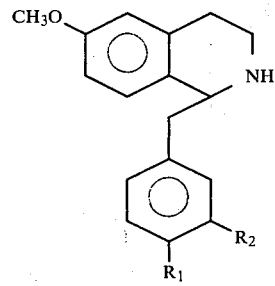

1'. $R_1 = CH_3O-$, $R_2 = -OH$
2'. $R_1 = R_2 = CH_3O-$
3'. $R_1, R_2 = CH_2\begin{smallmatrix}O-\\O-\end{smallmatrix}$ -continued

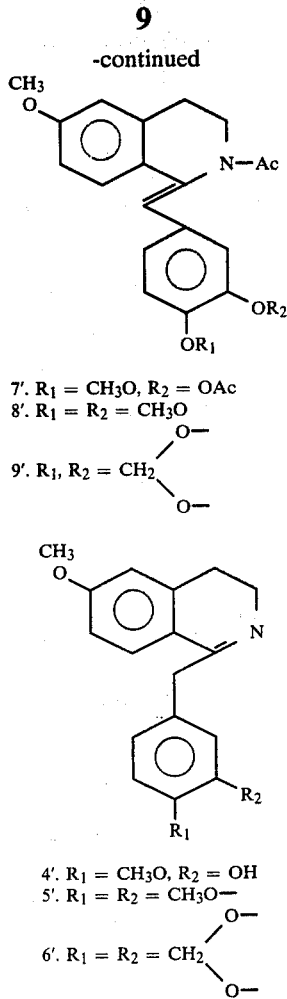

7'. $R_1 = CH_3O, R_2 = OAc$
8'. $R_1 = R_2 = CH_3O$
9'. $R_1, R_2 = CH_2\begin{smallmatrix}O-\\ \\O-\end{smallmatrix}$ 4'. $R_1 = CH_3O, R_2 = OH$
5'. $R_1 = R_2 = CH_3O$
6'. $R_1 = R_2 = CH_2\begin{smallmatrix}O-\\ \\O-\end{smallmatrix}$

DETAILS OF THE INVENTION

Suitable optical acids include (+)- and (−)-malic, tartaric and tartranilic acid.

For the malic and tartaric acids, alkanols of 1-6 carbon atoms are suitable solvents and methanol is the preferred solvent. Water may be added. Dimethyl formamide (DMF) is used to improve the yield.

For the tartranilic acid, acetonitrile and methanol are used as solvent and DMF acts to improve the yield.

For the tartaric acid, the procedure is as follows. To the racemate, (+)-tartaric acid in methanol at 55° C. is added. The mole ratio of base to acid is approximately 1:1. The (−)-1' base forms a salt that precipitates. The precipitate is heated to solution in DMF in which it is quite soluble and then diluted with methanol. The ratio of DMF to methanol is approximately 1:9. This method, based on a supersaturated solution, produces an almost quantitative yield. A second identical recrystallization is preferable to get a pure (−)-1'.(+)-tartaric salt, m.p. 134°-136° C.

The base (−)-1' is regenerated with aqueous 50% (v/v) methanol and concentrated aqueous ammonia. The solid base is washed with water, isopropanol and has the following properties: m.p. 218°-219.5° C. $[\alpha]_D^{23} - 37.7°$ (c 0.26 DMF).

The pooled filtrates are used to generate the (+)-1' base. The filtrates are evaporated, dissolved in 50% methanol at 55° C. with aqueous ammonia to generated mixed bases. This is the same procedure for regenerating all bases and the washings use water, isopropanol, and ether.

Using (−)-tartaric acid with the base (mole ratio of about 1:1 acid to base) in methanol gives a rapidly deposited crystalline material. Cooling and washing gives a (+)-1'.(−)-tartaric acid of approximately 99% optical purity. Recrystallization from a supersaturated solution of DMF with methanol added (1:9 volumes) gives a very good yield of the salt. The salt is converted to base following the above procedures. The optically pure base, (+)-1', has a m.p. 218.5°-220° C.; $[\alpha]_D^{23} +38.1°$ (c 0.27, DMF).

Chemical and optical purity is determined on HPLC as indicated in the examples.

The procedure with malic acid is similar to the above and similar results are obtained.

With nitrotartranilic acid, the (+)-2'-nitrotartranilic acid is used to precipitate a salt of (+)-1'.(+)-tartranilate. The solvent used is methanol first, then evaporation and acetonitrile. The volume of methanol to acetonitrile is 2-3:1. The precipitate is washed with acetonitrile.

The precipitate is recrystallized from a first solution of 1:1 DMF-CH₃CN (v/v), diluted with acetonitrile to give a very good yield. A second similar recrystallization is desirable. The salt (+)-1'.(+)-2'-nitrotartranilic has a m.p. of 195°-196.5° C. The regenerated base, (+)-1', has a m.p. of 217.5°-219° C. and $[\alpha]_D^{23} = +37.8°$ (c 0.25, DMF).

The filtrates and washing are treated as in resolution with tartaric acid to regenerate the bases. Treatment of the base with (−)-2'-nitrotartranilic acid in 1:1 DMF/acetonitrile and diluted with acetonitrile to give a good quantitative yield of (−)-1'.(−)-2'-nitrotartranilic acid salt with a m.p. of 193°-195° C. Regeneration of the base, (−)-1', gave a m.p. of 218°-219.5° C. and $[\alpha]_D^{23} = -38.1°$.

In the specification and claims the term alkanol means a $C_1$-$C_6$ alcohol and also may include water as an additive or alone.

The following examples illustrate the invention.

EXAMPLE 1

Optical Resolution of 1-(3-hydroxy-4-methoxybenzyl)-6-methoxy-1,2,3,4-tetrahydroisoquinoline (1')

A. With (+)- and (−)-tartaric acids.

Racemic 1' (59.87 g, 0.2 mol) was added in one portion to a stirred solution of 31.57 g (0.21 mol) of (+)-tartaric acid in 450 ml of MeOH at 55° C. to give a solution that rapidly deposited crystalline material. After keeping at 50°-55° C. for 5 minutes the mixture was cooled to 0°-5° C., filtered, washed with 250 ml of MeOH at 0° C. and dried to give 48.38 g of (−)-1'.(+)-tartaric acid in 93% optical purity. The (−)-1' from this salt was analyzed for optical purity by the method described below. This material was heated to solution in 43.5 ml of DMF (0.9 vol), diluted with 387 ml of MeOH (8 vol) and cooled to 0° C. to give (−)-1'.(+)-tartaric acid of 99% optical purity. A further recrystallization of this material by heating to solution in 0.9 volumes of DMF, diluting with 8 volumes of MeOH, cooling to 0° C. and washing with 250 ml of MeOH at 0° C. gave 42.49 g of chemically and optically pure (−)-1'.(+)-tartaric acid m.p. 134°-136° C. dec.

The base was regenerated by heating 42.49 g of this salt to solution in 640 ml of boiling 50% (v/v) aqueous MeOH and addition of 25 ml of concentrated aqueous NH₃ to rapidly give crystalline (−)-1'. Addition of 1.5 l of H₂O and filtration of the slurry (pH 9–9.5) afforded a solid which was washed well with H₂O, 2×50 ml of isopropanol and dried to give 26.11 g (87%) of (−)-1', m.p. 218°–219.5° C.; $[\alpha]_D^{23} -37.7°$ (c 0.26 DMF).

The pooled filtrates from above were evaporated, dissolved in 500 ml of 50% MeOH at 55° C. and treated with 35 ml of concentrated aqueous NH₃ to give crystalline mixed bases almost immediately. Addition of 1.5 l of H₂O, filtration and washing the solid successively with H₂O, 4×25 ml of isopropanol and 3×50 ml of Et₂O gave 32.60 g of mixed bases. This material was added to a solution of 17.15 g (0.11 mol) of (−)-tartaric acid in 450 ml of MeOH at 55° C. to give a solution that rapidly deposited crystalline material. After 10 minutes at 55° C., the mixture was cooled to 0° C. and washed with 250 ml of MeOH at 0° C. to give 46.96 g of (+)-1'.(−)-tartaric acid of 99% optical purity. Two crystallizations of this material by heating to solution in 0.9 vol of DMF and diluting with 8 vol of MeOH as above for the (−)-1'.(+)-tartarate gave 43.13 g of pure (+)-1'.(−)-tartrate. This salt was converted to 26.56 g (89%) of the pure (+)-base, m.p. 218.5°–220° C.; $[\alpha]_D^{23} = +38.1°$ (c 0.27, DMF).

Evaporation of the filtrate and washings from crystallization of this salt and treatment of a 1:1 MeOH-H₂O (v/v) solution with excess concentrated aqueous NH₃ as above for the optical isomers gave 5.25 g of recovered bases. This amounts to 97% accountability of the original (±)-1'.

General procedure for analysis of optical purity of 1-benzyl-1,2,3,4-tetrahydroisoquinolines The free base was regenerated from the tartrate salt. In the case of 1, 20 mg of the salt was heated to solution in 1 ml of 50% aqueous MeOH, and treated with 1 drop of concentrated aqueous NH₃. Dilution with H₂O, filtration and drying gave the base(s). A mixture of 5 mg of the base, 1 ml of dry THF and 8 μl of the appropriate isomer of optically and chemically pure α-methylbenzyl isocyanate were heated to solution, allowed to stand 10 minutes, and injected on HPLC (2 μPorasil columns (Waters Associates) in series, 92.1% isooctane, 7.2% isopropanol, 0.7% AcOH, 1.0 ml/min, U.V. detection at 260 nm. The chiral α-methyl benzyl isocyanate must be optically pure or lower than actual values will be obtained for optical purity.

B. With (+)- and (−)-2'-nitrotartranilic acids.

A mixture of 5.98 g (20 mmol) of racemate (±)-1' and 5.40 g of (+)-2'-nitrotartranilic acid were heated to solution in 250 ml of MeOH, evaporated and heated to solution in 100 ml of CH₃CN. Cooling to 20° C. afforded 4.43 g of (+)-1'.(+)-tartranilic acid, m.p. 190.5°–194.5° C. after washing with 50 ml CH₃CN. This salt was heated to solution in 20 ml of 1:1 DMF-CH₃CN (v/v), diluted with 75 ml of CH₃CN, cooled to 20° filtered and washed with CH₃CN to give 3.90 g of salt, m.p. 195°–196.5° C. An additional recrystallization as above gave 3.70 g of pure (+)-1'.(+)-2'-nitrotartranilic acid, m.p. 195°–196.5° C. Regeneration of the base as above for the tartrate salt gave 1.53 g of pure (+)-1', m.p. 217.5°–219° C. $[\alpha]_D^{23} +37.8°$ (c 0.25, DMF). The filtrate and washings from all recrystallizations above were evaporated to a sirup, heated to solution in 45 ml MeOH and rendered alkaline with 5 ml concentrated aqueous NH₃. After dilution with 200 ml of H₂O, filtration washing and drying gave 2.95 g of mixed bases m.p. 209.5°–215.5° C. This material was heated to solution with 2.65 g of (−)-2'-nitrotartranilic acid in 30 ml of 1:1 DMF acetonitrile and diluted with 75 ml CH₃CN. After keeping 15 minutes at 20° C., crystallization seemed complete and the solid material was filtered, washed with 50 ml CH₃CN and dried to give 4.53 g of (−)-1'.(−)-2'-nitrotartranilic acid m.p. 193°–195° C. Recrystallization of this salt as above afforded 4.20 g of pure (−)-1'.(−)-2'-nitrotartranilic acid m.p. 195°–196.5° C. Treatment of 3.51 g of this salt to liberate the free base identical to the above procedure for (+)-1' base gave pure (−)-1' base, m.p. 218°–219.5° C. $[\alpha]_D^{23} = -38.1°$.

I claim:

1. In a process for producing natural or unnatural morphine-type agonists and antagonists which includes a step producing a chiral hydroxy or lower alkoxy 1-benzyl-1,2,3,4-tetrahydroisoquinoline optically opposite from the desired optical morphine type and which comprises recycling the undesired optically opposite chiral lower alkoxy 1-benzyl-1,2,3,4-tetrahydroisoquinoline to a racemic mixture, the step which comprises oxidizing the chiral isoquinoline with hypohalide and base to produce an intermediate of 1-benzyl-1,2-dehydroisoquinoline and reduction of the dehydro intermediate to form a racemate of 1-benzyl-1,2,3,4-tetrahydroisoquinoline.

* * * * *